United States Patent [19]

Eicher et al.

[11] Patent Number: 5,283,381
[45] Date of Patent: Feb. 1, 1994

[54] PROCESS FOR PREPARING FLUORINE-CONTAINING ETHANE DERIVATIVES

[75] Inventors: Johannes Eicher, Garbsen; Karl-Heinz Fazniewscy, Lehrte; Werner Rudolph, Hannover, all of Fed. Rep. of Germany

[73] Assignee: Solvay Fluor und Derivate GmbH, Hannover, Fed. Rep. of Germany

[21] Appl. No.: 51,898

[22] Filed: Apr. 26, 1993

Related U.S. Application Data

[62] Division of Ser. No. 940,207, Sep. 8, 1992, Pat. No. 5,227,546.

[30] Foreign Application Priority Data

Sep. 14, 1991 [DE] Fed. Rep. of Germany ....... 4130696

[51] Int. Cl.⁵ .............................................. C07C 17/00
[52] U.S. Cl. ..................... 570/165; 502/150; 502/169; 570/166; 570/168
[58] Field of Search ................ 570/165, 166, 168; 502/150, 169

[56] References Cited

U.S. PATENT DOCUMENTS

| | | | |
|---|---|---|---|
| 4,258,225 | 3/1981 | Feiring | 570/168 |
| 4,374,289 | 2/1983 | Van Der Puy et al. | 570/168 |
| 4,383,128 | 5/1983 | Van Der Puy et al. | 570/165 |
| 4,967,024 | 10/1990 | Gumprecht et al. | 570/168 |
| 5,015,791 | 5/1991 | Rao | 570/168 |
| 5,214,223 | 5/1993 | Eicher et al. | 570/166 |
| 5,227,546 | 7/1993 | Eicher et al. | 570/165 |

FOREIGN PATENT DOCUMENTS

| | | | |
|---|---|---|---|
| 12614 | 12/1989 | World Int. Prop. O. | 570/168 |
| 12615 | 12/1989 | World Int. Prop. O. | 570/168 |
| 12616 | 12/1989 | World Int. Prop. O. | 570/168 |
| 12617 | 12/1989 | World Int. Prop. O. | 570/168 |

*Primary Examiner*—Werren B. Lone
*Attorney, Agent, or Firm*—Evenson, McKeown, Edwards & Lenahan

[57] ABSTRACT

A process for preparing fluorine-containing ethane derivatives using hydrogen fluoride and a catalytically active formulation comprising a tantalum fluorosulfonate compound or a niobium fluorosulfonate compound is described. The process is particularly suitable for preparing ethane derivatives which contain a $CF_3$ group, for example for preparing $CF_3CHCl_2$ (R123) from perchloroethylene.

1 Claim, No Drawings

PROCESS FOR PREPARING FLUORINE-CONTAINING ETHANE DERIVATIVES

This application is a division of application Ser. No. 07/940,207, filed Sept. 8, 1992 now U.S. Pat. No. 5,227,546.

BACKGROUND OF THE INVENTION

The invention relates to a process for preparing fluorine-containing ethane derivatives of the general formula $F_kCH_nCl_{3-(k+n)}CZ^1Z^2F$, wherein k, n, $Z^1$ and $Z^2$ have the meanings described below.

There is an increasing demand for environmentally compatible halohydrocarbons. Fluorine-containing ethane derivatives which contain at least one hydrogen atom, for example $CF_3CH_3$ (R143a), $CF_3CH_2Cl$ (R133a) and especially $CF_3CHCl_2$ (R123) and $CF_3CH_2F$ (R134a), for example, have proved to be such compounds. However, the corresponding 1-fluoro or 1,1-difluoro compounds are also of interest, for example the compounds $CFCl_2CHCl_2$ or $CF_2ClCHCl_2$, which are regarded as environmentally compatible and can be used as refrigerants, solvents or propellants.

Such compounds are prepared industrially from correspondingly halogenated derivatives by catalyzed halogen/fluorine exchange, particularly by chlorine/fluorine exchange. However, the halogenated starting compounds used here are very slow to react in a halogen/fluorine exchange.

In particular, drastic process conditions are needed to prepare more highly fluorinated compounds. In spite of such drastic conditions, for example working in the gas phase, the conversions are usually low. Another disadvantage of known processes is that the catalysts used, which are often very expensive, do not have a satisfactory life.

SUMMARY OF THE INVENTION

The object of the present invention is to provide a new process for preparing fluorine-containing ethane derivatives.

Another object of the invention is to provide a process for preparing fluorine-containing ethane derivatives which is easy to carry out industrially and has a high conversion.

These and other objects of the invention are achieved by providing a process for preparing a fluorine-containing ethane derivative corresponding to the formula I $$F_kH_nCl_{3-(k+n)}C\text{—}CZ^1Z^2F \qquad (I)$$

wherein $Z^1$ and $Z^2$ can be identical or different and denote hydrogen, fluorine, chlorine or bromine, k denotes 0, 1 or 2 and n denotes 1, 2 or 3, comprising catalytically reacting a starting compound selected from the group consisting of a) alkenes corresponding to the formula II $$F_kH_mCl_{2-k-m}C=CX^1X^2 \qquad (II)$$

wherein $X^1$ and $X^2$ can be identical or different and denote hydrogen, fluorine, chlorine or bromine, k has the aforementioned meaning and m denotes 0, 1 or 2, and b) halogen-containing alkanes corresponding to the formula III:

$$F_kH_nCl_{3-(k+n)}C\text{—}CY^1Y^2Y^3 \qquad (III)$$

wherein k and n have the above meaning, $Y^1$ and $Y^2$ can be identical or different and denote hydrogen, fluorine, chlorine or bromine and $Y^3$ denotes chlorine or bromine, with an at least equimolar amount of hydrogen fluoride in a liquid phase at a temperature of between 0° and 250° C. in the presence of a catalytically active formulation comprising at least one compound selected from the group consisting of tantalum fluorosulfonate and niobium fluorosulfonate, said formulation being essentially free of tantalum pentahalide and niobium pentahalide, wherein the molar ratio of starting compound to catalytically active compound is from about 10:1 to 1:100.

In accordance with a further aspect of the invention, the objects are achieved by providing a method of fluorinating a starting compound selected from the group consisting of alkenes corresponding to the formula $C_pH_aY_bF_c$ where Y is chlorine or bromine, p, a, b, and c are integers, at least one of a and b is other than zero, and $a+b+c=2p$, and alkanes corresponding to the formula $C_pH_aY_bF_c$ where Y, p, a, b and c have the meanings given above and $a+b+c=2p+2$, said method comprising reacting said starting compound with hydrogen fluoride in the presence of a catalytically effective amount of a catalyst corresponding to the formula $$MX_n(FSO_3)_{5-n} \qquad (IV)$$

wherein X is halogen, M is tantalum or niobium, and n is an integer from 0 to 4.

According to yet another aspect of the invention the objects are also achieved by providing a composition of matter for use in a fluorination reaction comprising a tantalum halide fluorosulfonate compound or a niobium halide fluorosulfonate compound corresponding to the formula IV $$MX_n(FSO_3)_{5-n} \qquad (IV)$$

and at least one compound selected from the group consisting of alkenes corresponding to the formula II $$F_kH_mCl_{2-k-m}C=CX^1X^2 \qquad (II)$$

wherein $X^1$ and $X^2$ can be identical or different and denote hydrogen, fluorine, chlorine or bromine, k has the aforementioned meaning and m denotes 0, 1 or 2; halogen-containing alkanes corresponding to the formula III $$F_kH_nCl_{3-(k+n)}C\text{—}CY^1Y^2Y^3 \qquad (III)$$

wherein k and n have the above meaning, $Y^1$ and $Y^2$ can be identical or different and denote hydrogen, fluorine, chlorine or bromine and $Y^3$ denotes chlorine or bromine; and hydrogen fluoride.

DETAILED DESCRIPTION OF PREFERRED EMBODIMENTS

The process according to the invention comprises the preparation of fluorine-containing ethane derivatives of the general formula (I)

$$F_kH_nCl_{3-(k+n)}C\text{—}CZ^1Z^2F \qquad (I)$$

wherein $Z^1$ and $Z^2$ can be identical or different and denote hydrogen, fluorine, chlorine or bromine, k denotes 0, 1 or 2 and n denotes 1, 2 or 3, by reaction of an alkene or halogen-containing alkane, as the starting compound, with hydrogen fluoride in a liquid phase at a temperature of between 0° and 250° C., the reaction being catalyzed by a catalytically active formulation comprising a tantalum fluorosulfonate compound and/or a niobium fluorosulfonate compound which is essentially free from tantalum pentahalide and/or niobium pentahalide, preferably essentially free from tantalum pentachloride and/or niobium pentachloride and tantalum pentabromide and/or niobium pentabromide, and the hydrogen fluoride being employed at least in the equimolar amount, based on the starting compound, the molar ratio of starting compound to catalytically active compound being between about 10:1 and 1:100, wherein a) a compound of the general formula (II)

$$F_k H_m Cl_{2-k-m} C=CX^1 X^2 \qquad (II)$$

wherein $X^1$ and $X^2$ can be identical or different and denote hydrogen, fluorine, chlorine or bromine, k denotes 0, 1 or 2 and m denotes 0, 1 or 2, is used as the alkene, or b) a compound of the general formula (III)

$$F_k H_n Cl_{3-(k-n)} C-CY^1 Y^2 Y^3 \qquad (III)$$

wherein k and n have the above meaning, $Y^1$ and $Y^2$ can be identical or different and denote hydrogen, fluorine, chlorine or bromine and $Y^3$ denotes chlorine or bromine, is used as the halogen-containing alkane.

Within the scope of the present invention, the sum of k and n is 1, 2 or 3, and the sum of k and m is 0, 1 or 2.

Preferably, in the starting compounds of the formula II and III, k represents 0 and $X^1$, $X^2$, $Y^1$ and $Y^2$ represent fluorine, chlorine or bromine.

The process can be carried out under pressures of between 1 and 100 bar (absolute) and at temperatures of 0° to 250° C., preferably 50° to 250° C. The pressure and temperature are chosen here so that the reaction proceeds in the liquid phase.

A tantalum halide fluorosulfonate compound or a niobium halide fluorosulfonate compound of the formula $MX_n(FSO_3)_{5-n}$, wherein X denotes halide, M denotes niobium or tantalum and n is 0 to 4, is preferably used as the catalytically active formulation. "Halide" here preferably denotes chloride or fluoride, in particular chloride, and n preferably denotes 1 to 4, in particular 2 to 4.

The preparation of such compounds is known. Thus E. Hayek, J. Puschmann and A. Czaloun in Monatsh. Chem. 85 (1954), pages 359 to 363 describe the preparation of $TaCl_3(FSO_3)_2$ from tantalum pentachloride and fluorosulfonic acid and evaporation of excess fluorosulfonic acid. The compound can also be prepared from tantalum pentachloride and fluorosulfonic acid derivatives, for example ethyl fluorosulfonate. Reaction products of niobium pentachloride and fluorosulfonic acid are viscous or gelatinous. In the view of the authors H. C. Clark and H. J. Emeleus in J. Chem. Soc. 1958, pages 190 to 195, in particular on page 193, the product is $NbCl_3(FSO_3)_2$.

In the same reference, Clark and Emeleus also describe the preparation of $TaF_3(FSO_3)_2$ and $NbF_3(FSO_3)_2$ from tantalum pentafluoride or niobium pentafluoride and sulfur trioxide at room temperature.

W. V. Cicha and F. Aubke in J. Fluorine Chem. 47 (1990), pages 317 to 332 describe the preparation of other tantalum fluoride fluorosulfonate and niobium fluoride fluorosulfonate compounds.

$Ta(FSO_3)_5$ and $Nb(FSO_3)_5$ can be prepared by oxidation of the particular metal powder with bis-(fluorosulfuryl) peroxide in fluorosulfonic acid. $NbF_2(FSO_3)_3$ is also formed as a by-product in the reaction of niobium metal powder.

$TaF_4(FSO_3)$ can be prepared, for example, by a ligand exchange reaction between $Ta(FSO_3)_5$ and 4 molar equivalents of tantalum pentafluoride.

As stated, a tantalum halide fluorosulfonate or niobium halide fluorosulfonate compound is preferably used. According to a particularly preferred embodiment, the catalytically active compound is a tantalum chloride fluorosulfonate compound or a niobium chloride fluorosulfonate compound which has been obtained by reaction of tantalum pentachloride or niobium pentachloride with fluorosulfonic acid in a molar ratio of 1:1 to 1:4. Instead of fluorosulfonic acid, it is also possible to use fluorosulfonic acid derivatives which react with tantalum pentachloride or niobium pentachloride, replacing chloride by fluorosulfonate, for example fluorosulfonic acid esters.

According to another particularly preferred embodiment, a tantalum fluoride fluorosulfonate compound or a niobium fluoride fluorosulfonate compound which has been obtained by reaction of tantalum pentafluoride or niobium pentafluoride with sulfur trioxide is used as the catalytically active compound. Alternatively, corresponding compounds which have been obtained by reaction of tantalum pentachloride or niobium pentachloride with fluorosulfonic acid or a fluorosulfonic acid derivative which reacts with tantalum pentachloride or niobium pentachloride, replacing chloride by fluorosulfonate, for example a fluorosulfonic acid ester, in a molar ratio of 1:1 to 1:4 and subsequent chlorine/fluorine exchange are used.

As stated, the process according to the invention is catalyzed by a catalytically active formulation which should be essentially free from tantalum pentahalide or niobium pentahalide. At the most, small undesirable amounts of such pentahalides are thus still present in the formulation.

If the expert uses a formulation which has been prepared by reaction of the niobium metal powder or tantalum metal powder in question with bis(fluorosulfuryl) peroxide in fluorosulfonic acid, the formulation is by nature free from pentahalide.

If the expert uses formulations which have been prepared by reaction of tantalum pentahalide or niobium pentahalide and fluorosulfonic acid, fluorosulfonic acid derivatives or sulfur trioxide, fluorosulfonic acid and the pentahalide are employed in a ratio of at least 1:1. The reaction between the alkene or alkane and hydrogen fluoride is only carried out when the tantalum pentahalide or niobium pentahalide and fluorosulfonic acid or a derivative of fluorosulfonic acid or sulfur trioxide have reacted to form the corresponding tantalum halide fluorosulfonate or niobium halide fluorosulfonate compound and the formulation is essentially free from pentahalide. This does not exclude the possibility that either the alkene or alkane to be (hydro)fluorinated or hydrogen fluoride is present in the reaction mixture before or during the reaction of niobium pentahalide or tantalum pentahalide to give the niobium halide fluorosulfonate or tantalum halide fluorosulfonate compound.

For example, niobium pentachloride or tantalum pentachloride and fluorosulfonic acid can be reacted with one another in the presence of the alkene or alkane to be (hydro)fluorinated. The organic compound then acts as a diluent. In this case, the hydrogen fluoride required for the hydrofluorination or the chlorine/fluorine exchange on the alkene or alkane is introduced only when the pentahalide for formation of the halide fluorosulfonate compound has essentially been consumed. The formulation should already be essentially free from tantalum pentahalide or niobium pentahalide at the start of the reaction between the alkene/alkane and hydrogen fluoride.

The ethane derivatives obtained in the process according to the invention differ from the starting compounds in that they contain at least one fluorine atom more. For each fluorine atom introduced into the substrate molecule in this manner, hydrogen fluoride is advantageously employed in an amount which corresponds to at least the stoichiometrically required amount. The amount of hydrogen fluoride used for HF addition or for the halogen/fluorine exchange can also be higher. It can be, for example, up to fifteen times or more the stoichiometrically required amount.

Good results are already achieved in the preparation of derivatives containing trifluoromethyl groups from unsaturated-compounds if the amount of hydrogen fluoride employed corresponds to one to ten times the stoichiometrically required amount.

The amount of hydrogen fluoride to be employed can exceed this amount which is required for hydrogen fluoride addition and/or the chlorine/fluorine exchange on the alkene or alkane. In fact, if Nb or Ta halide fluorosulfonate compounds which contain chloride or bromide are employed as a catalyst constituent, these metal halides are possibly present in the reaction mixture in the form of metal halide fluorosulfonates containing fluorine to a greater or lesser degree, due to exchange of chlorine or bromine for fluorine.

The statement made above on the amount of hydrogen fluoride to be employed is thus to be understood in the sense that for every fluorine atom introduced into the substrate molecule, hydrogen fluoride is advantageously employed in an amount which corresponds to at least the stoichiometrically required amount, and in addition an amount of hydrogen fluoride such as is required for any halogen/fluorine exchange of the halide in the metal halide fluorosulfonate. The statements made below concerning the stoichiometry of the hydrogen fluoride to be employed for the hydrogen fluoride addition and/or the halogen/fluorine exchange on the alkene or alkane are also to be interpreted in the same sense. For simplicity, the fact that additional hydrogen fluoride may be necessary for any halogen/fluorine exchange of the halide is not mentioned expressly each time in these statements.

In order to estimate the amount of hydrogen fluoride which will additionally be needed for this halogen/fluorine exchange, a person skilled in the art can pre-react the metal halide fluorosulfonate to be employed with hydrogen fluoride. The amount of hydrogen fluoride consumed and/or the amount of hydrogen halide formed enables the amount of hydrogen fluoride required, in addition to that required for the reaction of the halohydrocarbon which is used, to be calculated.

The following procedure is especially simple and advantageous: the metal halide, for example niobium pentachloride or pentabromide or tantalum pentachloride or pentabromide, is initially introduced into the fluorinating reactor, optionally in the presence of some or all of the organic starting compound to be fluorinated, and fluorosulfonic acid is added until no further hydrogen chloride or hydrogen bromide is evolved. Any remainder of the halohydrocarbon to be fluorinated and the hydrogen fluoride required for the fluorination are then passed into the catalyst mixture.

In order to prepare compounds having a low degree of fluorination, for example of $CHCl_2CCl_2F$ from $CHCl_2CCl_3$ or $CCl_2=CCl_2$, of $CH_2ClCCl_2F$ from $CH_2ClCCl_3$ or $CHCl=CCl_2$ or of $CH_3CCl_2F$ from $CH_3CCl_3$ or $CH_2=CCl_2$, it is advantageous to work in the lower temperature range, for example between 50° and 150° C. The degree of conversion can be monitored by analysis, for example by taking samples and analyzing them by gas chromatography.

The high degree of conversion of the process according to the invention is advantageous here.

Some examples of fluorine-containing ethane derivatives which can be prepared according to the invention are given in the following Table 1, in which the starting compounds which can be employed and the stoichiometrically required amount of hydrogen fluoride are listed.

TABLE 1

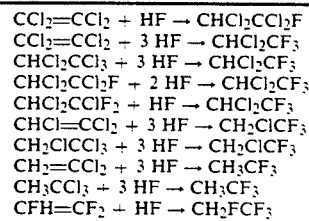

The advantages of the process according to the invention manifest themselves especially in the preparation of relatively highly fluorinated products. The preparation of relatively highly fluorinated products, for example the preparation of $CHCl_2CF_3$ from $CHCl_2CCl_3$, $CHCl_2CCl_2F$, $CHCl_2CClF_2$, $CCl_2=CCl_2$ or mixtures thereof, the preparation of $CH_2ClCF_3$ from $CH_2ClCCl_3$, $CH_2ClCCl_2F$, $CH_2ClCClF_2$, $CHCl=CCl_2$ or mixtures thereof, or the preparation of $CH_3CF_3$ from $CH_3CCl_3$, $CH_3CCl_2F$, $CH_3CClF_2$, $CH_2=CCl_2$ or mixtures thereof, is advantageously carried out in the higher temperature range, for example between 70° and 220° C. and under a pressure of 10 to 50 bar. In this case also the degree of conversion can be determined by analysis of samples taken from the reaction mixture.

The process according to the invention is therefore particularly advantageous for preparing relatively highly fluorinated compounds, in particular ethane derivatives, containing trifluoromethyl groups, of the general formula $F_kH_nCl_{3-(k+n)}C-CF_3$ (Ia), in which k denotes 0, 1 or 2 and n denotes 1, 2 or 3.

This preferred embodiment of the process according to the invention is characterized in that, to prepare fluorine-containing ethane derivatives of the general formula (Ia)

$$F_kH_nCl_{3-k+n}C-CF_3 \qquad (Ia)$$

wherein k denotes 0, 1 or 2 and n denotes 1, 2 or 3, at a temperature of 50° to 250° C. and under a pressure of 1 to 100 bar (absolute), a) a halogen-containing alkene of the general formula $$F_kH_mCl_{2-k-m}C=CX^1X^2 \quad (II)$$

wherein k and m have the aforementioned meaning and $X^1$ and $X^2$ denote fluorine, chlorine or bromine, is reacted with hydrogen fluoride, the hydrogen fluoride being employed in at least the stoichiometrically required amount for adding on the hydrogen fluoride and for the halogen-fluorine exchange on the alkene, or b) a halogen-containing alkane of the general formula $$F_kH_nCl_{3-(k+n)}C-CY^1Y^2Y^3 \quad (III)$$

wherein k and n have the aforementioned meaning, $Y^1$ and $Y^2$ denote fluorine, chlorine or bromine and $Y^3$ denotes chlorine or bromine, is reacted with hydrogen fluoride, the hydrogen fluoride being employed in at least the stoichiometrically required amount for the halogen/fluorine exchange on the alkane.

The advantages of the process according to the invention become particularly striking when the corresponding halogenated alkenes are used as the starting compound. The degree of conversion when these compounds, which are actually very slow to react, are used is very high. The formation of polymers or of compounds which are formed by addition of halogen other than by addition of hydrogen fluoride, which is observed with other processes, is at most observed in a negligibly small amount in the process according to the invention.

According to a preferred variant of the process according to the invention, halogenated alkenes are employed as the starting compounds. Hydrogen fluoride addition compounds are initially formed in a first reaction step. If the aim is to prepare such compounds having a low degree of fluorination, which indeed have useful properties, for example as solvents, these compounds are isolated from the reaction mixture. If the aim is to prepare more highly fluorinated products, in particular ethane derivatives containing trifluoromethyl groups, these compounds can be isolated, and fluorinated further. Advantageously, these hydrogen fluoride addition compounds formed intermediately in a first reaction step are not isolated, and these compounds are reacted in situ with further hydrogen fluoride to give the desired more highly fluorinated products.

At least partly fluorinated alkenes can also be used as starting materials. Thus, according to one embodiment of the process according to the invention, $CH_2FCF_3$ can be prepared by reacting trifluoroethylene with hydrogen fluoride in the presence of the metal halide fluorosulfonate. Surprisingly, no polymerization of the alkene is observed.

The process according to the invention is outstandingly suitable for preparing $CHCl_2CF_3$ (R123). This especially preferred embodiment of the process according to the invention is characterized in that, to prepare $CHCl_2CF_3$, a) $CCl_2=CCl_2$ is reacted with hydrogen fluoride, the hydrogen fluoride being employed in at least the stoichiometrically required amount for hydrogen fluoride addition and for the chlorine/fluorine exchange on the alkene, or b) $CHCl_2CCl_3$, $CHCl_2CFCl_2$, $CHCl_2CF_2Cl$ or mixtures thereof are reacted with hydrogen fluoride, the hydrogen fluoride being employed in at least the stoichiometrically required amount for the chlorine/fluorine exchange on the alkane.

The preparation of $CHCl_2CF_3$ from $CCl_2=CCl_2$ according to variant a) is especially preferred. The molar ratio of $CCl_2=CCl_2$ and hydrogen fluoride is advantageously between 1:3 and 1:100.

As stated above, the molar ratio of the starting compound to the metal fluorsulfonate compound is between 10:1 and 1:100.

The molar ratio of the starting compound to the metal fluorsulfonate compound is preferably between 10:1 and 1:10, particularly preferably between 2:1 and 1:5.

An especially preferred embodiment of the process is characterized in that, to prepare $CHCl_2CF_3$, $CCl_2=CCl_2$ is used as the starting substance, and this is reacted with at least the stoichiometrically required amount of hydrogen fluoride for hydrogen fluoride addition and for the chloride/fluorine exchange on the alkene, the reaction product of the reaction of niobium pentahalide, tantalum pentahalide or mixtures of these compounds with fluorosulfonic acid in a molar ratio of 1:1 to 1:3 being employed as the catalytically active formulation.

Moisture interferes with the process according to the invention. The reaction is therefore advantageously carried out under conditions which prevent a harmful amount of water from being able to enter the reaction mixture. Essentially anhydrous hydrogen fluoride is used. Depending on the amount of hydrogen fluoride employed, it may be advisable to dry commercially available hydrogen fluoride before its use. It is furthermore advisable to keep the apparatus used in the driest possible state. For this purpose, the lines, reaction vessels and equipment for working up and storing the product can be flushed with dry gases, for example with dry air or dry nitrogen gas.

The reaction can be carried out as a batch process or continuously. At least the stoichiometrically required amount of hydrogen fluoride for the halogen/fluorine exchange or for hydrogen fluoride addition should always be present in the reaction mixture. The reaction mixture can be worked up by passage through a gas washer and subsequent fractional distillation.

The apparatus used for carrying out the process should be resistant to hydrogen fluoride. Components of Teflon and special alloys, such as "Hastelloy", a nickel alloy which is resistant to hydrogen fluoride, are advantageously used.

The invention furthermore relates to the use of metal fluorosulfonate compounds of the general formula (IV)

$$MX_n(FSO_3)_{5-n} \quad (IV)$$

in which X denotes halogen and n denotes 0 to 4, as a catalyst. X preferably denotes chlorine or fluorine, and n preferably denotes 1 to 4, in particular 2 to 4.

The preparation is carried out as described above, from the pentahalides with fluorosulfonic acid or fluorosulfonic acid derivatives, for example fluorosulfonic acid esters. If chlorides are used as starting substances, the reaction product can be reacted with hydrogen fluoride, if desired, to give the corresponding fluoride fluorosulfonate. If fluorides are used as starting materials, corresponding metal fluoride fluorosulfonates are also obtained in the reaction with sulfur trioxide.

The invention furthermore relates to formulations for use in the process of the invention which comprise a tantalum halide fluorosulfonate or niobium halide fluorosulfonate compound of the formula (IV) and either an alkene of the formula (II), an alkane of the formula (III) or hydrogen fluoride, the sum of the constituents being 100% by weight. These formulation, which preferably comprise 0.1 to 99% by weight, in particular 10 to 90 and especially preferably 30 to 70% by weight of the compound of the formula (IV) are obtainable by mixing the individual constituents. If desired, any hydrogen chloride or hydrogen bromide formed can be separated out.

The fluorine-containing ethane derivatives obtained by the process of the invention are useful environmentally compatible solvents, propellants and intermediate products for chemical synthesis.

The process according to the invention is distinguished by a high conversion and high selectivity, and it can advantageously be carried out in the liquid phase.

The high efficiency of the process according to the invention must be regarded as surprising and unpredictable. In fact, if, for example, perchloroethylene is employed as the starting compound and fluorosulfonic acid is employed as the catalyst, the conversion is negligibly small. Niobium pentachloride as the catalyst produces lower degrees of conversion. It is therefore completely unpredictable that, for example, the reaction product of these catalyst constituents, which in themselves are almost unusable, leads to such good results in respect of degree of conversion, selectivity and life of the catalyst mixture in the process according to the invention, and also allows the preparation of relatively highly fluorinated products, such as, in particular, R123.

The following examples are intended to illustrate the process according to the invention in more detail, without limiting its scope.

EXAMPLES

Example 1: Preparation of Trifluorodichloroethane (R123) and Difluorotrichloroethane (R122) from Tetrachloroethylene Using a Tantalum Halide Fluorosulfonate Compound 1.1. Apparatus used:

The reaction was carried out in a reactor, which can be closed, of HF-resistant material (Hastelloy C4 TM, an alloyed steel). The reactor has an internal volume of 2 liters. It is provided with a blade stirrer, a reflux condenser, thermoconnectors and inlet tubes (the internal temperature can be measured via the thermoconnectors). The reflux condenser is connected to a gas washer filled with water. The gas washer in turn is connected to a cryogenic condensation device.

1.2. Preparation of the tantalum halide fluorosulfonate compound.

720 g of tantalum pentachloride (2 moles) and 230 g of fluorosulfonic acid (2.3 moles) were introduced into the reactor via inlet tubes. The reactor was then closed. The reaction mixture was stirred at room temperature, during which the pressure in the reactor rose to 5 bar. 240 g of hydrogen fluoride (12 moles) were then also forced into the reactor. The contents of the reactor were then stirred once again at room temperature. Constituents which were gaseous at room temperature were then released from the reactor via the reflux condenser and passed through the gas washer. The gaseous constituents essentially consisted of HCl. As analysis of the contents of the gas washer showed, the wash solution contained the entire chlorine content, in the form of hydrochloric acid, of the tantalum pentachloride introduced. It is therefore assumed that the tantalum in the formulation prepared in the reactor was essentially present in the form of $TaF_4(FSO_3)$ in hydrogen fluoride.

1.3. Procedure for preparing R123 and R122.

Hydrogen fluoride and tetrachloroethylene were passed into the formulation comprising hydrogen fluoride and tantalum fluoride fluorosulfonate prepared in step 1.2. The metering was regulated such that 50 g of hydrogen fluoride (2.5 moles) and 50 ml of tetrachloroethylene (0.5 mole) were metered in per hour. The temperature in the reaction mixture was regulated to 145° C., and the pressure was regulated to 13 to 15 bar by means of a regulating valve. A total of 4 kg of hydrogen fluoride and 4.2 kg of perchloroethylene were metered in.

An adequate amount of the low-boiling constituents were continuously released from the reactor in gaseous form via the reflux condenser and passed through the washer, and the organic constituents leaving the washer were condensed in the cryogenic condensation device. A total of 3300 g of organic constituents were condensed in the cryogenic condensation device.

The composition in percent by weight of the organic phase was determined by gas chromatography to be:

R124 ($C_2HClF_4$) : 0.1%
R123 ($C_2HCl_2F_3$) : 38.2%
R122 ($C_2HCl_3F_2$) : 60.3%
R121 ($C_2HCl_4F$) : 0.2%
$C_2Cl_4$ : 0.9%

Example 2: Semi-continuous Preparation of Trifluorodichloroethane 2.1. Apparatus used.

A laboratory autoclave of V4A steel (a steel alloyed with chromium, nickel and molybdenum) was used. The internal volume of this autoclave is 0.25 liter. The autoclave was equipped with a magnetic stirrer, an immersion tube through which the starting compounds could be metered in, and a thermoconnector for measuring the internal temperature. The laboratory autoclave furthermore had a gas discharge connected to a gas washer filled with water. The gas washer in turn was connected to a cryogenic condensation device.

2.2. Preparation of the niobium halide fluorosulfonate compound and experimental procedure.

27 g of niobium pentachloride (0. 1 mole) and 10 g of fluorosulfonic acid were introduced into the autoclave. Before the addition of 40 g of tetrachloroethylene (0.24 mole), the hydrogen chloride which forms during the formation of the niobium chloride fluorosulfonate compound was released. 40 g of hydrogen fluoride were then metered in three portions. Between each addition, the excess pressure formed was released by venting highly volatile constituents.

The autoclave was then closed and subjected to a first heating phase. For this, the contents of the autoclave were brought to the temperature shown in Table 2 and were kept at this temperature for the period of time shown in Table 2. The contents of the autoclave were then brought to ambient temperature and the hydrogen chloride formed was released. A sample of the compounds which are volatile at ambient temperature under normal pressure was then taken and analyzed by gas chromatography to determine the organic compounds contained therein. The analyzed values, stated in % by weight, are listed in Table 2.

The contents of the autoclave were then subjected to a second heating phase. After cooling, the reactor was brought to normal pressure, and this time the total content of compounds which are volatile at room temperature under normal pressure were released from the reactor and passed through the gas washer. The crude product leaving the gas washer was analyzed by gas chromatography.

Into the reactor, in which the catalyst system and also organic compounds of low volatility remained, were metered 40 g of tetrachloroethylene and 40 g of hydrogen fluoride. The reactor was then subjected to a third heating phase and cooled, the hydrogen chloride formed was released, and a sample of the organic compounds which are volatile at the ambient temperature under normal pressure was then analyzed. Thereafter, the reaction was subjected to a fourth heating phase and cooled, and the total content of compounds which are volatile at about room temperature under normal pressure was passed from the reactor into the gas washer, and the crude product leaving the gas washer was again analyzed by gas chromatography.

This procedure was repeated several times. After each of the second (see above), fourth and sixth heating phases, 40 g of hydrogen fluoride and 40 g of tetrachloroethylene were introduced into the reactor. The maximum temperature established in each heating phase, the maximum pressure reached and the period over which the maximum temperature was maintained, as well as the data from the gas chromatography analysis of the gas phase obtained after each heating phase are summarized in the following Table 2:

TABLE 2

| Heating phase | Maximum temperature | Maximum pressure | Duration in hours | R22 | R23 | R122 | R123 |
|---|---|---|---|---|---|---|---|
| 1 | 160° C. | 34 bar | 3.5 | — | — | 38.9% | 58.7% |
| 2 | 170° C. | 19 bar | 4.0 | — | 0.1% | 16.7% | 81.2% |
| 3 | 160° C. | 17 bar | 3.0 | 4.5% | 2.6% | 14.6% | 76.0% |
| 4 | 170° C. | 33 bar | 4.5 | 1.5% | 2.6% | 18.4% | 75.4% |
| 5 | 170° C. | 26 bar | 5.0 | 1.3% | 2.8% | 31.4% | 62.1% |
| 6[a] | 165° C. | 28 bar | 5.5 | 0.9% | 2.4% | 17.9% | 59.8% |
| 7[b] | 160° C. | 15 bar | 6.0 | 0.5% | 0.6% | 21.7% | 56.3% |
| 8[c] | 165° C. | 17 bar | 5.0 | — | — | — | 69.6% |

"%" denotes "% by weight"
[a]also 16.8% of R123a
[b]also 19.2% of R123a
[c]also 28.2% of R123a Between 0.2 and 0.8% of R124 and between 0.2 and 0.5% of R125 were also found during the gas chromatography analysis.

Example 3: Semi-continuous Preparation of R123 and R122 from Tetrachloroethylene.

3.1. Apparatus used.

The apparatus described under Example 2.1. was used.

3.2. Preparation of a catalytically active formulation comprising a tantalum halide fluorosulfonate compound.

40 g of tetrachloroethylene, 36 g (0.1 mole) of tantalum pentachloride and 30 g (0.3 mole) of fluorosulfonic acid were initially introduced into the autoclave in this sequence (in this case the tetrachloroethylene acted as a diluent). The autoclave was closed and the contents of the autoclave were stirred. During the stirring operation, a pressure of about 5 bar built up. This pressure was released via the regulating valve. A formulation which comprised the tantalum chloride fluorosulfonate compound formed and tetrachloroethylene was then present.

3.3. Experimental procedure.

40 g of hydrogen fluoride were metered into the formulation prepared in step 3.2. During the stirring operation, the pressure rose to about 12 bar. The pressure was released via the regulating valve.

In a first heating phase, the contents of the reactor were heated up to 160° C. over the course of one hour and kept at this temperature for 4 hours. The pressure rose to 32 bar during this operation. After cooling, the low-boiling constituents were analyzed by gas chromatography. The analytical result is summarized in Table 3.

Before a second heating phase, 20 g of tetrachloroethylene and 20 g of hydrogen fluoride were introduced into the autoclave. A total of eight heating phases were carried out in an analogous manner. Between the heating phases, the low-boiling constituents were analyzed by gas chromatography (the analytical result of the seventh heating phase was distorted), and in each case 20 g of tetrachloroethylene and 20 g of hydrogen fluoride were introduced into the autoclaves (only 20 g of hydrogen fluoride and no tetrachloroethylene before the sixth heating phase). A total of 180 g of tetrachloroethylene and 200 g of hydrogen fluoride were employed. The process parameters and the analytical result of the individual heating phases (up to the seventh heating phase) are summarized in Table 3.

When the last heating phase was completed, the reaction mixture which remained in the autoclave was poured onto ice, and 74 g of an organic phase which separated was removed. This organic phase was also analyzed by gas chromatography. 40 g of the tetrachloroethylene employed were recovered in this way.

It was possible to calculate from the analytical results that the total of 140 g of tetrachloroethylene which had been reacted in the course of the semi-continuous process had essentially been converted into R123 (70%), R122 (25%) and R121 (5%).

TABLE 3

| Heating phase | Maximum temperature | Maximum pressure | Duration in hours | R22 | R23 | R122 | R123 |
|---|---|---|---|---|---|---|---|
| 1 | 160° C. | 32 bar | 6 | 4.1% | 1.7% | 1.4% | 91.4% |
| 2 | 160° C. | 22 bar | 3 | 1% | 4% | 4.5% | 90% |
| 3 | 164° C. | 23 bar | 4.5 | 0.6% | 0.6% | 29.3% | 67.8% |
| 4 | 163° C. | 18 bar | 3.5 | 0.4% | 1.1% | 16.8% | 79.7% |
| 5 | 160° C. | 16 bar | 2 | 0.4% | 1.4% | 12.7% | 82.6% |
| 6[a] | 160° C. | 16 bar | 4.5 | —% | —% | —% | |
| 7[b] | 160° C. | 16 bar | 3.5 | 0.4% | —% | 2.3% | 64.3% |
| 8[c] | 160° C. | 15 bar | 6 | 1.2% | 0.3% | 26.4% | 65.6% |
| residue | — | — | — | — | — | 29.8% | [d]0.4% |

"%" denotes "% by weight"
[a]gas chromatography sample distorted
[b]also 31% of R23/CO₂, 1.1% of R22 and 0.3% of R1112
[c]also 4.5% of R1112 and 0.3% of R113
[d]also 41.6% of tetrachloroethylene and 27.6% of R121

The content of relatively highly fluorinated ethanes, in particular trifluorodichloroethane and difluorotrichloroethane, is also still very good in the continuous or semicontinuous procedure even after a long reaction time because of the stability of the catalyst.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all variations falling within the ambit of the appended claims and equivalents thereof.

What is claimed is:

1. A composition of matter for use as a reaction mixture in a fluorination reaction comprising a tantalum halide fluorosulfonate compound or a niobium halide fluorosulfonate compound corresponding to the formula IV $$MX_n(FSO_3)_{5-n} \qquad (IV)$$

and at least one compound selected from the group consisting of alkenes corresponding to the formula II $$F_kH_mCl_{2-k-m}C=CX^1X^2 \qquad (II)$$

wherein $X^1$ and $X^2$ can be identical or different and denote hydrogen, fluorine, chlorine or bromine, k has the aforementioned meaning and m denotes 0, 1 or 2; halogen-containing alkanes corresponding to the formula III $$F_kH_nCl_{3-(k-n)}C—CY^1Y^2Y^3 \qquad (III)$$

wherein k and n have the above meaning, $Y^1$ and $Y^2$ can be identical or different and denote hydrogen, fluorine, chlorine or bromine and $Y^3$ denotes chlorine or bromine; and hydrogen fluoride.

* * * * *